United States Patent [19]
Mihashi

[11] Patent Number: 5,929,970
[45] Date of Patent: Jul. 27, 1999

[54] OPTICAL CHARACTERISTIC MEASURING APPARATUS

[75] Inventor: Toshifumi Mihashi, Tokyo, Japan

[73] Assignee: Kabushiki Kaisha Topcon, Tokyo, Japan

[21] Appl. No.: 09/078,049

[22] Filed: May 13, 1998

Related U.S. Application Data

[30] Foreign Application Priority Data

May 13, 1997 [JP] Japan .................................. 9-137630

[51] Int. Cl.$^6$ ...................................................... A61B 3/00
[52] U.S. Cl. ............................................................ 351/205
[58] Field of Search ..................................... 351/205, 206, 351/211, 212; 359/629, 630, 633

[56] References Cited

U.S. PATENT DOCUMENTS

| | | | |
|---|---|---|---|
| 4,598,984 | 7/1986 | Rol | 351/219 |
| 5,768,025 | 6/1998 | Togino et al. | 359/633 |

Primary Examiner—George Manuel
Attorney, Agent, or Firm—Baker & Botts, L.L.P.

[57] ABSTRACT

In the present invention, an illuminating optical system illuminates an infinitesimal domain on an object to be examined using light rays emitted from an illuminating light source, a light receiving optical system receives light rays reflected back from the object to be examined and guides the reflected light rays to a light receiving unit, a converting member separates the reflected light rays into at least five regions and, in the regions, converges the light rays through a converging operation and transmits the light rays through a transmitting operation, the light receiving unit receives a plurality of light rays converted at the converting member, a display unit forms an image of the object to be examined on the basis of the light rays which have undergone the transmitting operation from the converting member and have been obtained at the light receiving unit, and an optical characteristic arithmetic unit determines optical characteristics of the object to be examined on the basis of an inclination angle of the light rays which have undergone the converging operation from the converting member and have been obtained at the light receiving unit.

10 Claims, 9 Drawing Sheets

REGULAR ASTIGMATISM

IRREGULAR ASTIGMATISM

OPTICAL CHARACTERISTIC MEASURING APPARATUS

BACKGROUND OF THE INVENTION

The present invention relates to an apparatus for precisely measuring optical characteristics of an object to be examined, and to an optical characteristic measuring apparatus for allowing an observation of the object to be examined as well as for measuring the optical characteristics of the object to be examined. More particularly, when the object to be examined is a human eye, the present invention relates to an optical characteristic measuring apparatus which makes it possible to observe a front eye part of the eye to be examined as well as to measure optical characteristics of an irregular astigmatism component of the eye.

A conventional optical characteristic measuring apparatus for measuring the optical characteristics of the eye known as a refractometer is capable of expressing the optical characteristics of the eye merely as a spherical component, a regular astigmatism component and the angle of the axis of the regular astigmatism component.

Some eyes have an irregular astigmatism component in addition to a regular astigmatism component. Irregular astigmatism cannot be corrected by spectacles if the quantity of the irregular astigmatism component is large, contact lens must be used instead of a pair of spectacles lens, and the eye must be examined by a medical doctor.

A prior art apparatus for measuring the optical characteristics of the eye to be examined, however, could be used only for correcting eyeglasses, which was not so satisfactory.

Accordingly, desired strongly was an appearance of an optical characteristic measuring apparatus, which makes it possible to accurately measure the irregular astigmatism component of an object to be examined, to say nothing of a spherical component and a regular astigmatism component thereof and an axis angle of the regular astigmatism component, as well as makes it possible to observe the object to be examined with the use of only one light receiving device.

SUMMARY OF THE INVENTION

In the present invention, an illuminating optical system illuminates an infinitesimal domain on an object to be examined using light rays emitted from an illuminating light source, a light receiving optical system receives light rays reflected back from the object to be examined and guides the reflected light rays to a light receiving unit, a converting member separates the reflected light rays into at least five regions and, in the regions, converges the light rays through a converging operation and transmits the light rays through a transmitting operation, the light receiving unit receives a plurality of light rays converted at the converting member, a display unit forms an image of the object to be examined on the basis of the light rays which have undergone the transmitting operation from the converting member and have been obtained at the light receiving unit, and an optical characteristic arithmetic unit determines optical characteristics of the object to be examined on the basis of an inclination angle of the light rays which have undergone the converging operation from the converting member and have been obtained at the light receiving unit.

DETAILED DESCRIPTION OF THE PREFERRED EMBODIMENTS

First Embodiment

Figure 1A:
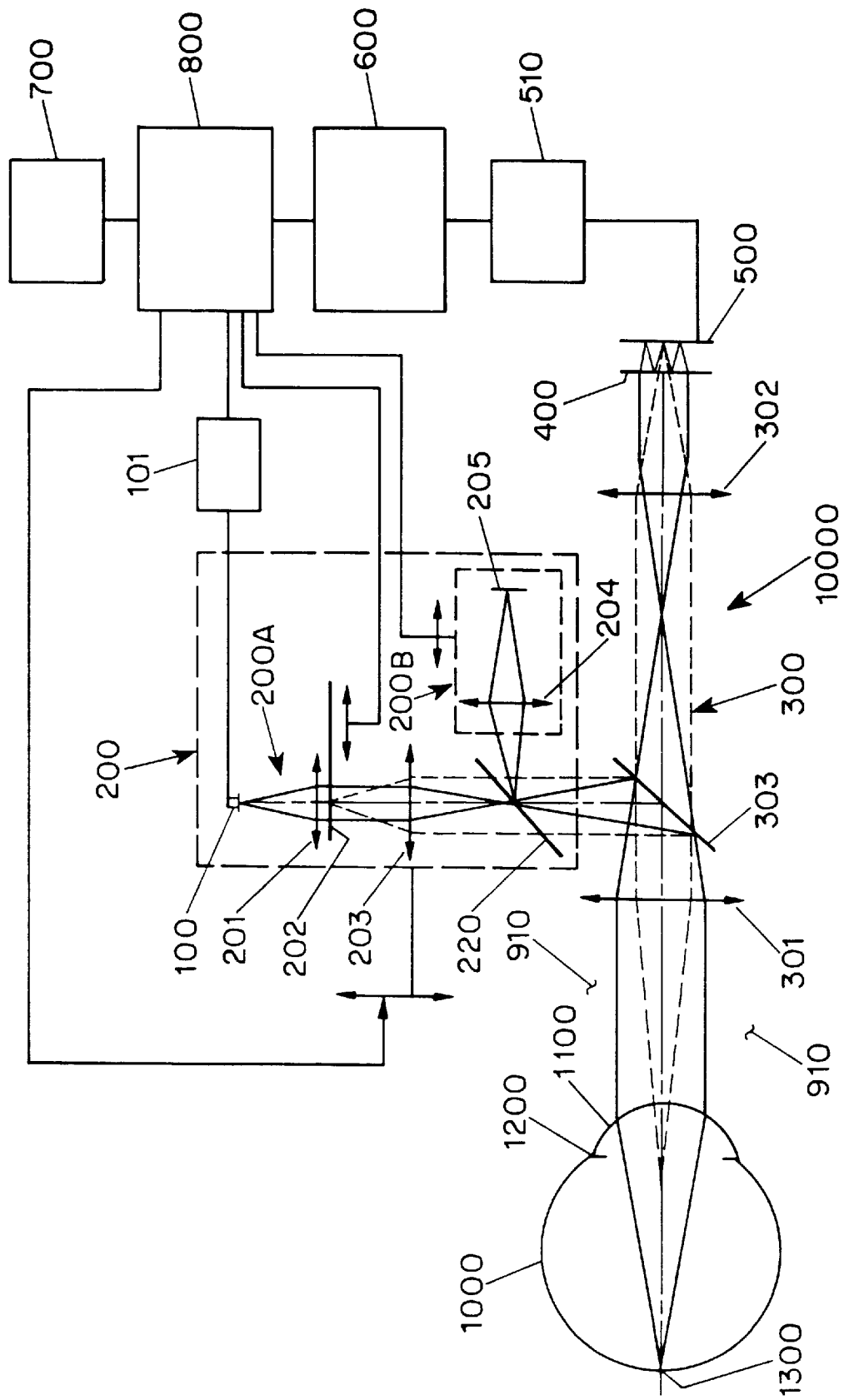
FIG. 1A is a block diagram of an optical characteristic measuring apparatus in a first embodiment according to the present invention.

Referring to FIG. 1A, an optical characteristic measuring apparatus in a first embodiment according to the present invention comprises an illuminating light source 100, an illuminating optical system 200 for illuminating a minute region on the retina of the eye 1000 with light rays emitted by the light source 100, a light receiving device 500 which receives light rays reflected from the retina of the eye 1000, a reflected light guiding optical system 300 for guiding light rays reflected from the retina of the eye to the light receiving device 500, a converting device 400 which converts the reflected light rays into at least seventeen light beams which are received by the light receiving device 500, an an optical characteristic calculating unit 600 which determines the optical characteristics of the eye 1000 on the basis of the inclinations of the light beams determined by the light receiving device 500.

A controller 800 controls operations of the whole electrical configuration of the optical characteristic measuring apparatus including the optical characteristic calculating unit 600. The controller 800 controls and drives the light source 100 through a light source driving unit 101.

It is desirable that the light source 100 is capable of emitting light having a high spatial coherence and a low temporal coherence. The light source 100 of the first embodiment is a SLD (Super Luminescent Diode), which is a point light source having a high luminance.

The light source 100 need not be limited to the SLD (Super Luminescent Diode); a laser which emits light having a high spatial coherence and a high temporal coherence can be employed as the light source 100 if a rotary diffuser or the like is inserted in an optical path to lower the temporal coherence properly.

Although both the spatial coherence and the temporal coherence of the light emitted by a light source such as LED are low, it can be used if a pinhole or the like is disposed at a position corresponding to the light source on the light path, provided that it emits a large quantity of light.

The wavelength of the light emitted by the illuminating light source 100 of the first embodiment may be equal to, for example, that of the E line at the middle of the visible region. Although it is desirable to use the ● line (546.07 nm), which is a reference wavelength for spectacles, for measurement, the d line (587.56 nm) may be used for measurement when the optical characteristic measuring apparatus is used in the USA.

The illuminating optical system 200 illuminates a minute region on the retina with the light rays emitted by the light source 100. The illuminating optical system 200 comprises a first condenser lens 201, a variable diaphragm 202, a second condenser lens 203, a fixation point focusing lens 204, and a fixation point 205.

Figure 1B:
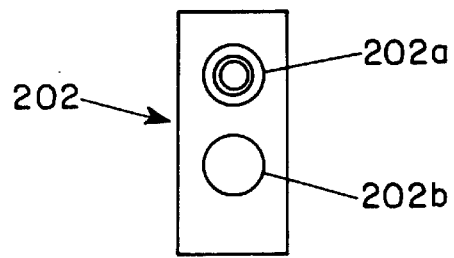
FIG. 1B is a front view of a variable diaphragm included in the optical characteristic measuring apparatus of FIG. 1.

The variable diaphragm 202 is a light screening member. As shown in FIG. 1B, the variable diaphragm 202 is provided with a first diaphragm 202a having an aperture in its peripheral portion, and a second diaphragm 202b having an aperture in its central portion. The first diaphragm 202a and the second diaphragm 202b are arranged side by side. The variable diaphragm 202 is moved in directions perpendicular to its optical axis by a signal provided by the controller 800 to dispose either the first diaphragm 202a or the second diaphragm 202b on the optical path.

Accordingly, the variable diaphragm 202 of the illuminating optical system 200 is able to create a first illuminating state for illumination through a region around the center of the pupil of the eye 1000 and a second illuminating state for illumination through the periphery of the pupil of the eye 1000 at a point substantially conjugate with the pupil of the eye 1000.

The eye 1000 has the cornea 1100, the iris 1200 and the retina 1300.

The variable diaphragm 202 reduces the influence of light reflected by the cornea on measurement.

The reflected light guiding optical system 300 guides the light rays reflected from the retina 1300 of the eye 1000 to the light receiving device 500. The reflected light guiding optical system 300 comprises a first afocal lens 301, a second afocal lens 302, a converting device 400 which converts the reflected light rays into at least seventeen light beams, and a beam splitter 303. The light receiving device 500 of the reflected light guiding optical system 300 is conjugate with the variable diaphragm 202 of the illuminating optical system 200. The light receiving device 500 and the variable diaphragm 202 are conjugate with the iris 1200.

The light reflected from the cornea can be prevented from affecting the measurement of refraction by using a screened portion of the illuminating optical system 200 for the measurement of refraction.

If the first diaphragm 202a of the variable diaphragm 202 is on the optical path, a region corresponding to the central screening portion of the first diaphragm 202a is measured. If the second diaphragm 202b is disposed on the optical path, a region corresponding to a portion around the central aperture is measured.

The illuminating optical system 200 is constructed so that a minute region on the eyeground of the eye 1000 is illuminated by the light emitted by the light source 100 according to the refracting power of the eye 1000. The abnormal refraction of the eye 1000 can be corrected by moving a point light source illuminating system 200A for projecting the light emitted by the light source 100, and an illuminating system including a fixation point projecting system 200B.

The point light source illuminating system 200A comprises the first condenser lens 201, the variable diaphragm 202 and the second condenser lens 203. The fixation point projecting system 200B comprises the fixation point focusing lens 204 and the fixation point 205. Light rays emitted by the point light source illuminating system 200A and light rays emitted by the fixation point projecting system 200B are combined in coaxial light rays by a beam splitter 220.

The conjugate relationship between the light source 100 and the fixation point 205 is maintained. The illuminating optical system 200 is moved to form images of the point light source and the fixation point 205 on the retina 1300, and then the fixation point projecting system 200B is moved slightly away from the beam splitter 220 by a signal provided by the controller 800 to blur the image of the fixation point 205.

A first diopter adjusting mechanism adjusts the diopters of the point light source illuminating system 200A and the fixation point projecting system 200B by moving the variable diaphragm 202 and the fixation point 205 respectively along their optical axes so that the level of light received by the light receiving device 500 is kept at a maximum.

One of the objects of the optical characteristic measuring apparatus 10000 in the first embodiment is the measurement of optical characteristics in a state having a specific refractive power at the far point of accommodation, the near point of accommodation or a point between the far point of accommodation and the near point of accommodation.

Accordingly, a minute region on the eyeground is illuminated with light rays according to the variation of the refractive power of the eyes 1000 because, in measurement at the far point of accommodation, for instance, the refractive powers of the eyes 1000 vary in the range of −25D to 25D (Diopter). Therefore, the light source 100, the point light source illuminating system 200A and the fixation point projecting system 200B are moved by signals provided by the controller 800.

Also, the light receiving optical system 300 comprises the first afocal lens 301, the second afocal lens 302, the converting member 400, and the light receiving device 500. When the eye to be examined is positioned at an appropriate operating distance, the following relation is satisfied.

Namely, a front side focus of the first afocal lens 301 substantially coincides with a front eye part of the eye to be examined, i.e. an object to be examined. Moreover, the front eye part of the eye to be examined is substantially in a conjugate relationship with the light receiving device 500 through the first afocal lens 301 and the second afocal lens 302.

The illuminating optical system 200 and the light receiving optical system 300 are configured as follows. Assuming that light rays emitted from the light source 100 are reflected at points at which the light rays are gathered, the illuminating optical system 200 and the light receiving optical system 300, maintaining a relation that a signal peak by the reflected light rays becomes its maximum at the light receiving unit 500, move in a coupled manner, move towards a direction in which the signal peak by the reflected light becomes stronger at the light receiving unit 500, and stop at a position at which the intensity becomes its maximum. This eventually allows the light rays from the light source 100 to be gathered on the eye to be examined.

The converting device 400 will be described hereinafter. The converting device 400 included in the reflected light guiding optical system 300 is a wavefront converting device which converts the reflected light rays into a plurality of light beams. The converting device 400 has a plurality of micro Fresnel lenses arranged in a plane perpendicular to the optical axis.

The micro Fresnel lens will be described in detail.

A micro Fresnel lens is an optical element having annular bands at height pitches for wavelengths and an optimized blaze at a focal point. A micro Fresnel lens which can be applied to the present invention has, for example, eight levels of optical path differences produced by semiconductor fine processing techniques, and is capable of achieving focusing at a focusing efficiency of 40% when only primary light is used.

As a result, launched into the light receiving unit 500 are a first-order light provided by a micro Fresnel lens corresponding to the converting member 400 as light rays indicating optical characteristics of the eye to be examined, and a zero-order light provided by the micro Fresnel lens as an image of the front eye part of the eye to be examined.

When the light source 100 is being switched on continuously, received at the same time at the light receiving unit are the light rays for measuring the optical characteristics and the light rays of the front eye part of the eye to be examined, i.e. the object to be examined. Accordingly, the image of the front eye part of the eye to be examined, i.e. the object to be examined, is formed on a display unit 700 in a state in which the points, at which the light rays for measuring the optical characteristics are gathered, are contained discretely.

Also, when the light source 100 is flashed on and off, an image of only the front eye part of the eye to be examined, at the time of extinguishing the light source, is formed at the light receiving unit and is displayed by the display unit 700. During a time period when the optical characteristics are being measured, the image of the front eye part of the eye to be examined can also be displayed by storing it in a buffer memory.

This makes it possible to form the image of the front eye part of the eye to be examined, i.e. the object to be examined, which contains no light rays for measuring the optical characteristics. This situation can be said to be more desirable.

Meanwhile, reflected light rays from eyegrounds pass through the first afocal lens 301 and the second afocal lens 302, and are gathered on the light receiving unit 500 as the first-order light thereof through the converting member 400. Here, the zero-order light corresponds to transmitting light rays and the first-order light corresponds to converging light rays.

Incidentally, when measuring the spherical component S, the cylindrical component C, and the axis angle component A, it becomes necessary to determine five or more of higher-order aberrations other than these components.

Also, the converting member 400 can be configured by a micro lens part for performing the converging operation and an aperture part for performing the transmitting operation in each region of the reflected light rays separated into at least five regions.

The converting member 400 according to the present first embodiment is constituted by a wave front converting member for converting the reflected light rays into at least seventeen or more of light beams.

The light receiving device 500 receives a plurality of light beams from the converting device 400. In the first embodiment, the light receiving device 500 is a CCD. The CCD may be a common CCD for TV use or a CCD having 2000×2000 elements for measurement use.

Although a CCD for TV use as the light receiving device 500 has a low resolution, the CCD for TV use is inexpensive and its output can be easily given to a personal computer which is used generally for image processing. NTSC image signals provided by a CCD and its driver can be easily given to a personal computer through an NTSC image input port.

Although a CCD for measurement use having 2000×2000 elements is expensive, analog signals representing measured values can be given to a personal computer if a CCD for measurement use is employed.

Signals provided by a CCD can be converted into corresponding digital signals, and the digital signals may be given to a personal computer.

The reflected light guiding optical system 300 establishes substantially conjugate relationship between the iris 1200 of the eye 1000 and the converting device 400.

The beam splitter 303 is inserted in the reflected light guiding optical system 300 to direct the light transmitted by the illuminating optical system 200 toward the eye 1000, and to transmit the reflected light.

An image signal provided by the light receiving device 500 is given through a light receiving device driver 510 to the optical characteristic calculating unit 600.

The principle of operation of the optical characteristic calculating unit 600 which calculates the optical characteristics of the eye 1000 on the basis of the inclination of light rays determined by the light receiving device 500 will be described hereinafter.

"No relay lens and immovable: Optical characteristics including spherical component are measured"

Emmetropia: Parallel light rays are focused on the eyeground to make a secondary light source on the eyeground emit parallel light rays.

Myopia: Convergent light rays are emitted.

Regular astigmatism: Astigmatism is measured.

Irregular astigmatism: High-order aberration is mixed.

A method of calculation will be described in detail.

Figure 2:
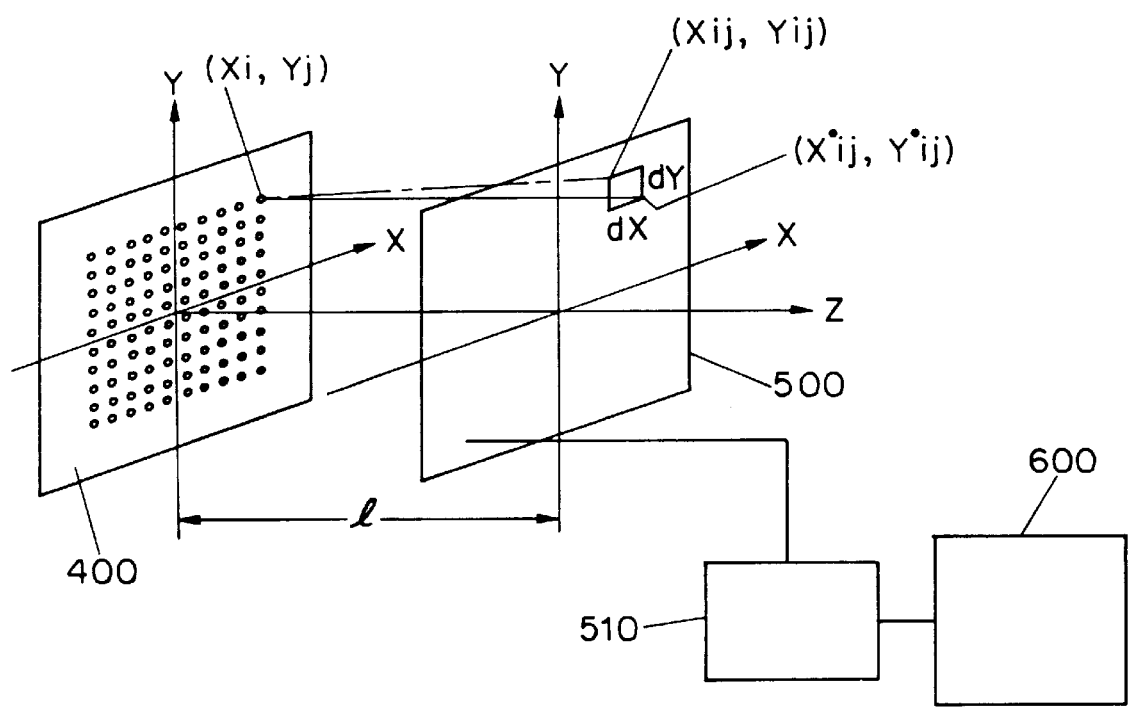
FIG. 2 is diagrammatic view of assistance in explaining the principle of the optical characteristic measuring apparatus of FIG. 1.

As shown in FIG. 2, coordinate axes X and Y are set on the converting device, and coordinate axes x and y are set on the light receiving device 500. Then, a wave surface is expressed by a polar coordinate system or a rectangular coordinate system:

$$w(r, \theta) = W(X, Y) \tag{1}$$

The (i, j)-th measured data is expressed by:

$$w(r_i, \theta_j) = W(X_i, Y_j) \tag{2}$$

The contents of the measured data will be explained later.

The wave surface is expressed by an approximate expression:

$$F(K, G, T, S, C, A, X, Y) = \text{Constant } (K) + \text{Inclination } (G, T, X, Y) + \text{Spherical surface } (S, X, Y) + \text{Regular astigmatism } (C, A, X, Y) \tag{3}$$

The components of this polynomial will be explained.

The constant term is K.

The inclination reflecting alignment error is:

$$Gr\cos(\theta - T) = G\cos(T)X + G\sin(T)Y \tag{4}$$

Spherical surface (Discussion concerning sign)

$$S \pm \sqrt{S^2 - r^2} = S \pm \sqrt{S^2 - (X^2 + Y^2)} \quad (5)$$

Sign is "+" when S is negative and sign is "−" when S is positive.

Regular astigmatism (Discussion concerning sign)

Formula 2 (6)

$$(C^2 \pm \sqrt{C^2 - r^2})\cos^2(\theta + A) =$$
$$(C \pm \sqrt{C^2 - (X^2 + Y^2)}) \left( \frac{\cos^2(A)X^2 + 2\sin(A)\cos(A)XY + \sin^2(A)Y^2}{X^2 + Y^2} \right)$$

Sign is "+" when C is negative and sign is "−" when C is positive.

The square sum of the residuals at each measurement point is:

$$\sum_{i,j} [W(X_i, Y_j) - F(K, G, T, S, C, A, X_i, Y_j)]^2 \quad (7)$$

Values of K, G, T, S, C and A are determined so that a value calculated by Formula 3 is a minimum. The suffixes i and j denotes one of the elements of the converting device 400. Practically, the data represents inclinations and hence the derivative of each wave surface is used for calculation because data measured by the optical characteristic measuring apparatus are the inclination of light rays.

The inclination of light rays can be directly determined by the differentiation of the wave surface by positional coordinates. Values measured by the wavefront sensor are transverse aberrations from a reference.

It is generally known that the following relation holds approximately in FIG. 2.

$$\frac{\partial W(X, Y)}{\partial X} = \frac{dx(X, Y)}{l} \quad (8)$$

$$\frac{\partial W(X, Y)}{\partial Y} = \frac{dy(X, Y)}{l} \quad (9)$$

where l is the distance between the converting device 400 and the light receiving device 500.

"Wave surface, and transverse aberration measured by the wavefront sensor"

Values dx(X, Y) and dy(X, Y) are calculated for each element of the converting device 400, having a center point at X, Y, in which dx and dy are distances along the x-axis and the y-axis between a predetermined origin on the light receiving device 500, and a point on the light receiving device 500 where the light beam falls on the light receiving device 500. As shown in FIG. 2, an origin corresponding to one element of the converting device 400 is a point on the light receiving device 500 where the converted light rays can be measured when both the spherical component and the astigmatism component representing the refractive characteristic of the eye are 0 diopter, and there is no residual of irregular astigmatism, which will be described later.

Suppose that the position of each point is $(x^0, y^0)$ when S, C and A are zero and there is no residual aberration. Then, $$dx(X_i, Y_j) = x_{ij} - x^0_{ij} \quad (10)$$

$$dy(X_i, Y_j) = y_{ij} - y^0_{ij} \quad (11)$$

Therefore, at the time of using the differentiation, the square sum of the residuals is:

$$\sum_{i,j} \left[ \left\{ \frac{dx(X_i, Y_j)}{l} - \left( \frac{\partial F}{\partial X} \right)_{(X_i, Y_j)} \right\}^2 + \left\{ \frac{dy(X_i, Y_j)}{l} - \left( \frac{\partial F}{\partial Y} \right)_{(X_i, Y_j)} \right\}^2 \right] \quad (12)$$

The parameters G, T, S and C of F which makes the residual a minimum may be determined by an appropriate nonlinear optimizing method, such as a method of attenuation least squares.

The values of K, G and T are considered to reflect measuring errors. In an auto-refractometer, S, C and A are measured values.

Although signs of some terms in the expressions expressing a spherical surface and regular astigmatism are indefinite, combinations may be calculated individually and a case where the residual is the smallest may be employed.

A Irregular Astigmatism Component

The differentiation residuals are irregular astigmatism component.

The conventional auto-refractometer is unable to measure the residual component, and a new piece of software is necessary.

When analyzing the residual, i.e., the irregular astigmatism component, (1) The residual is calculated and represented in the form of the square sum.

(2) The residual is divided into components by a method similar to a method known in the theory of aberration.

(3) All the deviations from the wave surface expressed by S, C and A as a reference surface are provided.

In some cases, a reference wave surface expressed by S or a reference wave surface represented by a plane is necessary to find out the distortion of the wave surface if the irregular astigmatism is large.

"Square Sum of Residuals"

The square sum of residuals is measured by using K, G, T, S, C and A determined by the foregoing method. If the square sum of residuals has N rows and M columns, a measurement value of the square sum of residuals is obtained by dividing the square sum of residuals by a value obtained by doubling the square of n=N×M.

$$\frac{\sum_{i,j} \left[ \left\{ \frac{dx(X_i, Y_j)}{l} - \left( \frac{\partial F}{\partial X} \right)_{(X_i, Y_j)} \right\}^2 + \left\{ \frac{dy(X_i, Y_j)}{l} - \left( \frac{\partial F}{\partial Y} \right)_{(X_i, Y_j)} \right\}^2 \right]}{2n} \quad (16)$$

B Analysis of Components

Comatic aberration: $r^{(2n+1)} \cos(\theta + T_n)$ (n=1, 2, ...)
Spherical aberration: $r^{2n}$ (n=2, 3, ...)
High-order astigmatism: $r^{2n} \cos^2(\theta + A_n)$ (n=1, 2, ...)

There is an important aberration of an order higher than that of the astigmatism component in the direction of rotation $f(r) \cos^n (\theta+T_n)$ (n=3, . . . )

The parameters of these terms are determined by subtracting values contributed to the components of the inclination, the spherical surface and the regular astigmatism by G, T, S, C and A obtained previously from the inclination of light rays. The comatic aberration, the spherical aberration, the high-order astigmatism and other contribution can be calculated.

C Output of Deviation from Reference Wave Surface

A distance between corresponding positions on the reference wave surface $W_b$ and the actual wave surface $W_r$ is indicated.

In the following description, Fb and Fr are obtained by removing terms of constants and inclination from F.

These are expressed by functions approximating wave surfaces.

(Reference wave surface)=$W_b(X_i, Y_j)=F_b(S, C, A, X_i, Y_j)$
(Reconstructed wave surface)=$W_r(X_i, Y_j)=F_r(S, C, A,$ parameters of irregular astigmatism component, $X_i, Y_j)$ $$\Delta z_{ij} = W_r(X_i, Y_j) - W_b(X_i, Y_j) \quad (17)$$

All the indications can be expressed in a unit of wavelength or a unit of micrometer.

D Indication of Deviation of Power from Reference Wave Surface (1) Power is calculated on the basis of the respective calculated residuals of the components.

(2) The inclination dependent only the residual component at that point is determined on the basis of only the residual component.

(3) The inclination at that point calculated on the basis of the reference wave surface Wb is subtracted from the measured value, and the power of a point is calculated on the basis of points, typically, eight or fifteen points, around the point.

Figure 3:
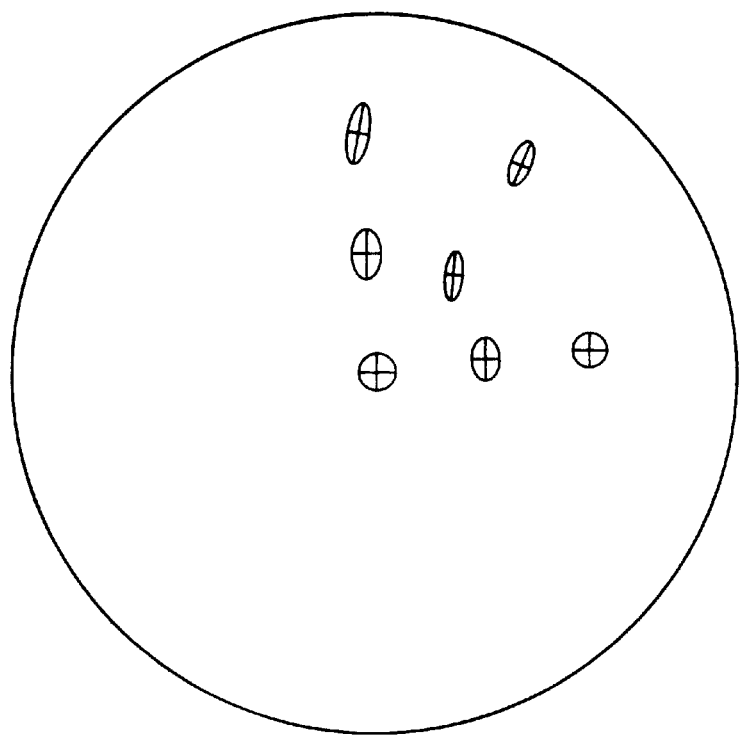
FIG. 3 is a diagrammatic view of assistance in explaining a method of directly indicating power based on quantity and orientation relating to maximum curvature and minimum curvature.

As shown in FIG. 3, the power indicates directly a quantity and an orientation relating to the maximum and the minimum curvature at a point on a geometrical curved surface. When light rays converge in a radius R of curvature, power is expressed by 1/R.

Figure 4:
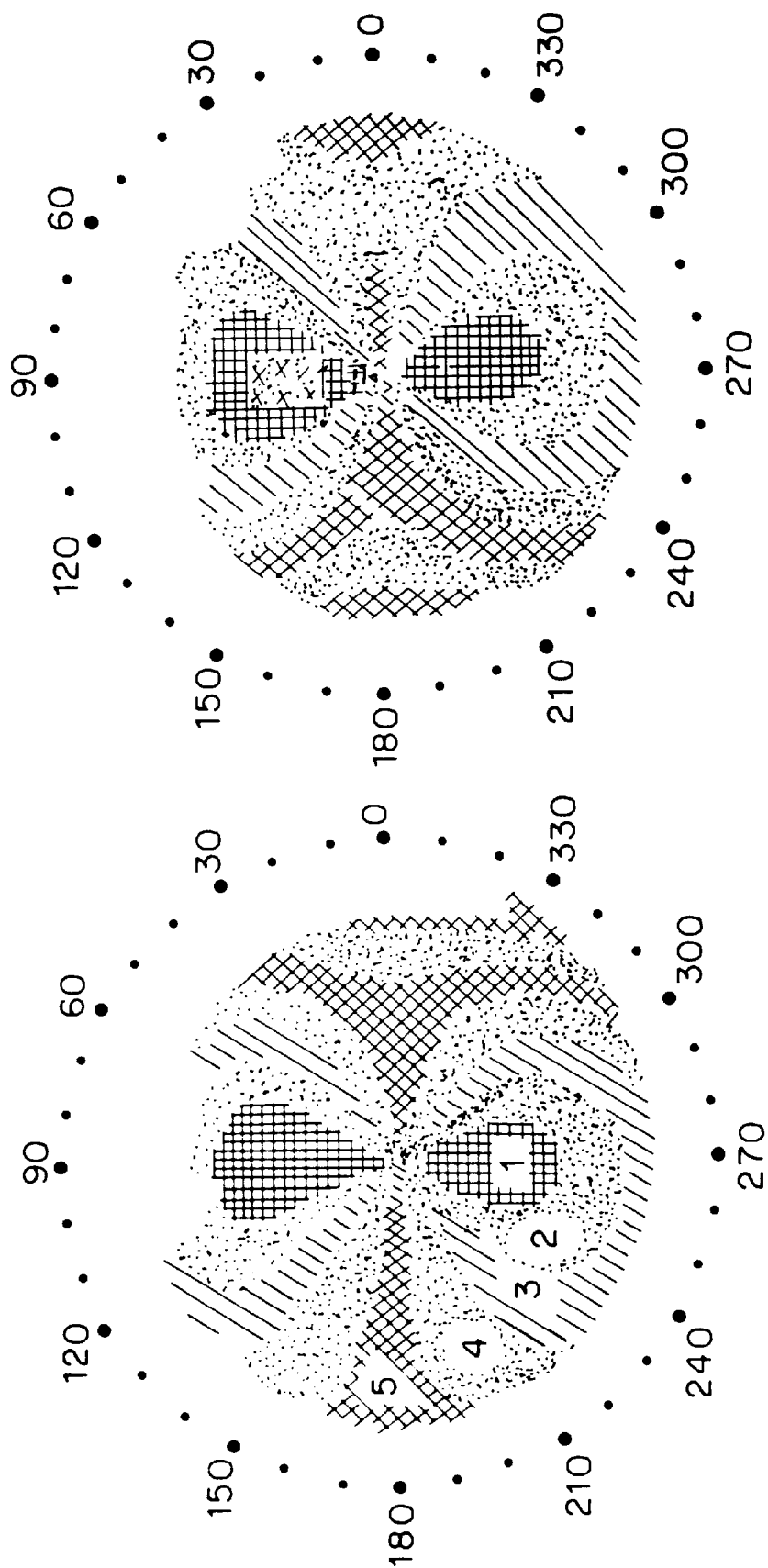
FIG. 4 is a pictorial view of assistance in explaining a method of indicating meridional power.
Figure 5:
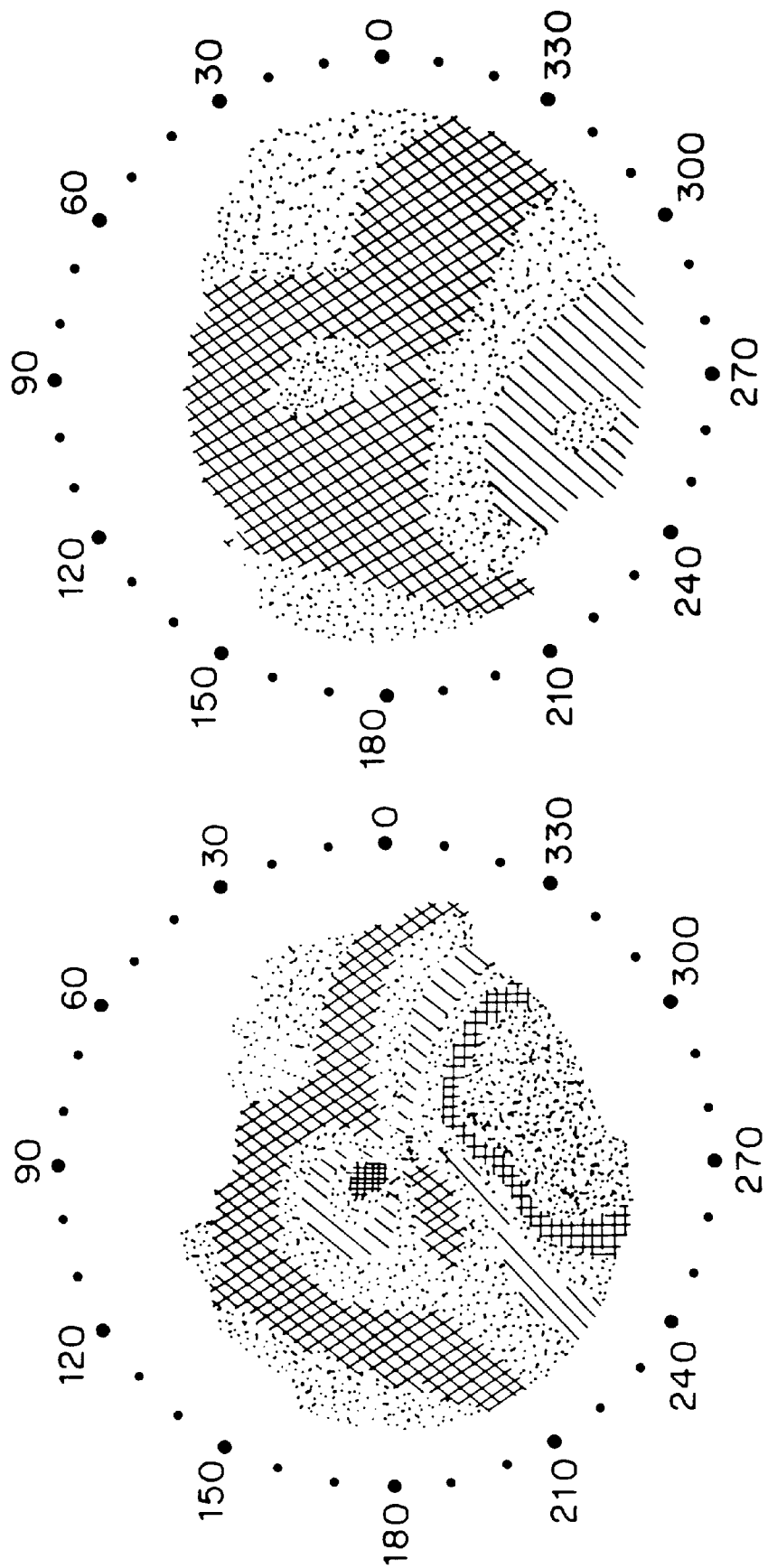
FIG. 5 is a pictorial view of assistance in explaining a method of indicating meridional power.

Meridional power is indicated by a method illustrated in FIGS. 4 and 5.

Generally, regular astigmatism has a high power in the direction of the vertical meridian and a low power in the direction of the horizontal meridian. Power is expressed in diopters.

The operation of the converting device 400 for converting the reflected light rays into at least seventeen light beams will be described in detail.

It is possible to calculate measurement values, as long as they are measurement values of the spherical component S, the cylindrical component C, and the axis angle component A, by using at least five points of data which consist of the point of origin and four points lying in different four radial directions. Moreover, if there is need of information on data which are at least one order higher than the five points of data, the number of the measuring points, through a summation of 2 * 8=16 and the point of origin, turns out to be at least seventeen or more.

Accordingly, the optical characteristic calculating unit 600 determines the inclination of light rays from a position on which the primary light rays are converged by the plurality of micro Fresnel lenses, and determines the optical characteristics of the eye 1000 on the basis of the inclination of light rays.

A blurred image is formed at one point represented by data on received light rays if the converting device 400 does not use the micro Fresnel lenses, and hence the center of gravity of each point is determined.

Figure 6:
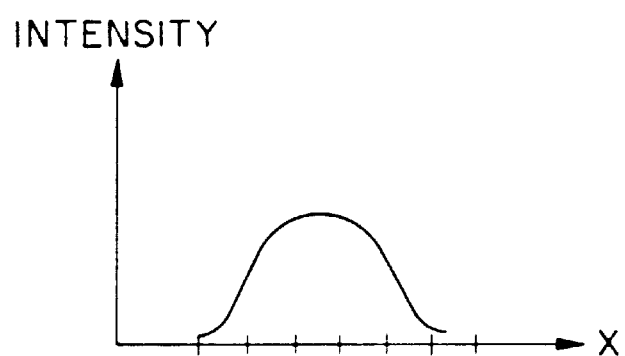
FIG. 6 is a graph of assistance in explaining a method of improving the accuracy of position measurement.

Even if micro Fresnel lenses are used, the accuracy of position measurement can be increased by observing an image intentionally blurred by the light receiving elements as shown in FIG. 6. The position of the center of gravity can be determined by making the projected light rays fall on a plurality of pixels on the light receiving surface and making reference to the intensities of light rays fallen on the pixels.

The accuracy of position measurement not higher than $\frac{1}{10}$ of the element can be secured by thus calculating the position of the center of gravity.

The optical characteristic measuring apparatus may be provided with a display unit 700 for displaying the results of arithmetic operations carried out by the optical characteristic calculating unit 600.

The display unit 700 are capable of displaying the optical characteristics of the eye 1000 in the spherical component, the regular astigmatism component, the angle of the axis of the regular astigmatism component, and the irregular astigmatism component, which are determined by calculation by the optical characteristic calculating unit 600.

Examples will be given below.

(1) Display of irregular astigmatism component

The irregular astigmatism component indicates a comatic component, a spherical aberration component and a high-order astigmatism component.

(2) Display of irregular astigmatism component as deviation

The irregular astigmatism component indicates two-dimensionally deviation from the wave surface consisting of only a spherical component and a regular astigmatism component.

(3) Two-dimensional display of curvature of wave surface in diopters

Two-dimensional graphic display is possible. A point having astigmatism has two curvatures. According to the teachings of differential geometry, both are perpendicular to each other.

The display unit 700 is capable of graphically displaying the optical characteristics of the eye 1000. The display unit 700 is capable of displaying a picture of the eye 1000 viewed from the front on an x-y coordinate system and of mapping powers in, for example, diopters on an x-y coordinate system.

The display unit 700 is capable of displaying the deviations of the optical characteristics of the eye 1000 from those of the normal eye.

The display unit 700 is also capable of mapping the deviations from a reference wave surface reproduced from the calculated values of S, C and A on the order of wavelength on the x-y coordinate system.

The display unit 700 is capable of graphically displaying deviations of the optical characteristics of the eye 1000 from those of the normal eye, and those data can be represented in contour.

The display represented in contour can be mapped by, for example, pseudocolors.

Figure 7A:
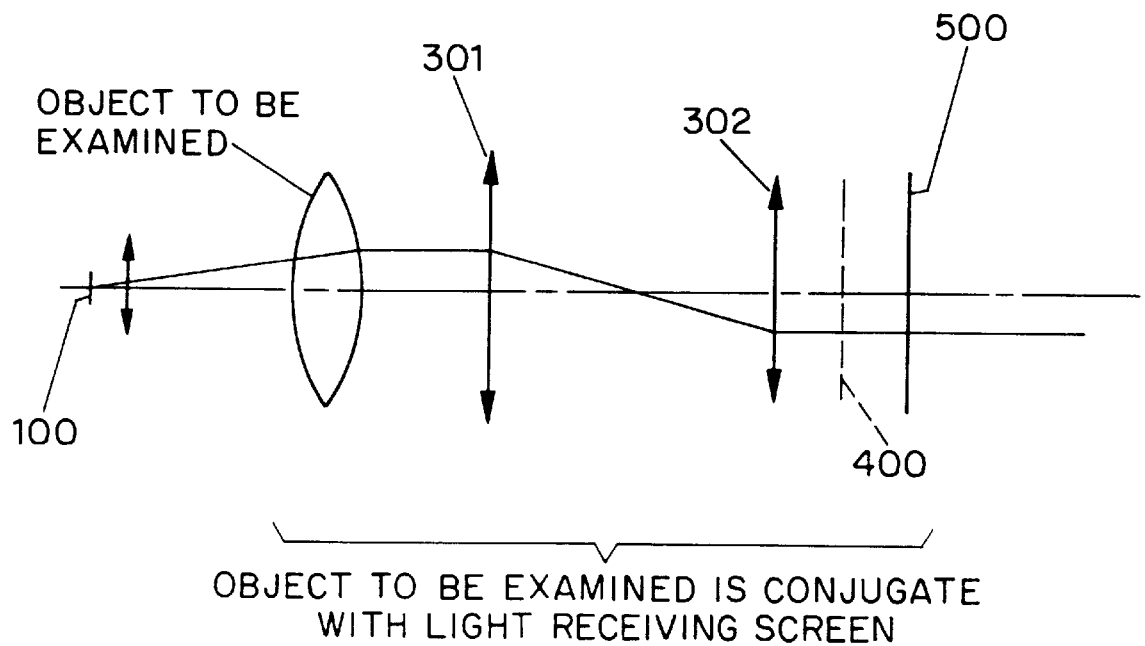
FIG. 7(A), FIG. 7(B), and FIG. 7(C) are diagrams for explaining an alignment.
Figure 7C:
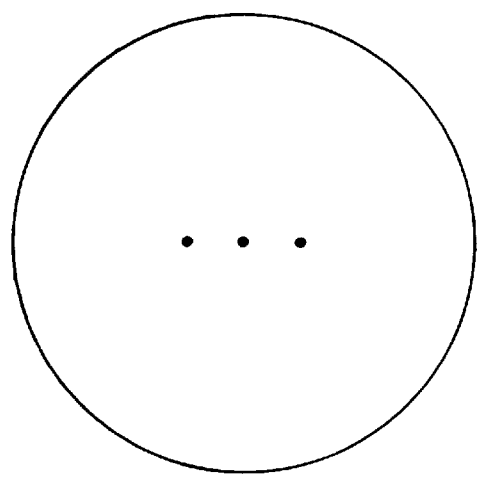
Figure 7B:
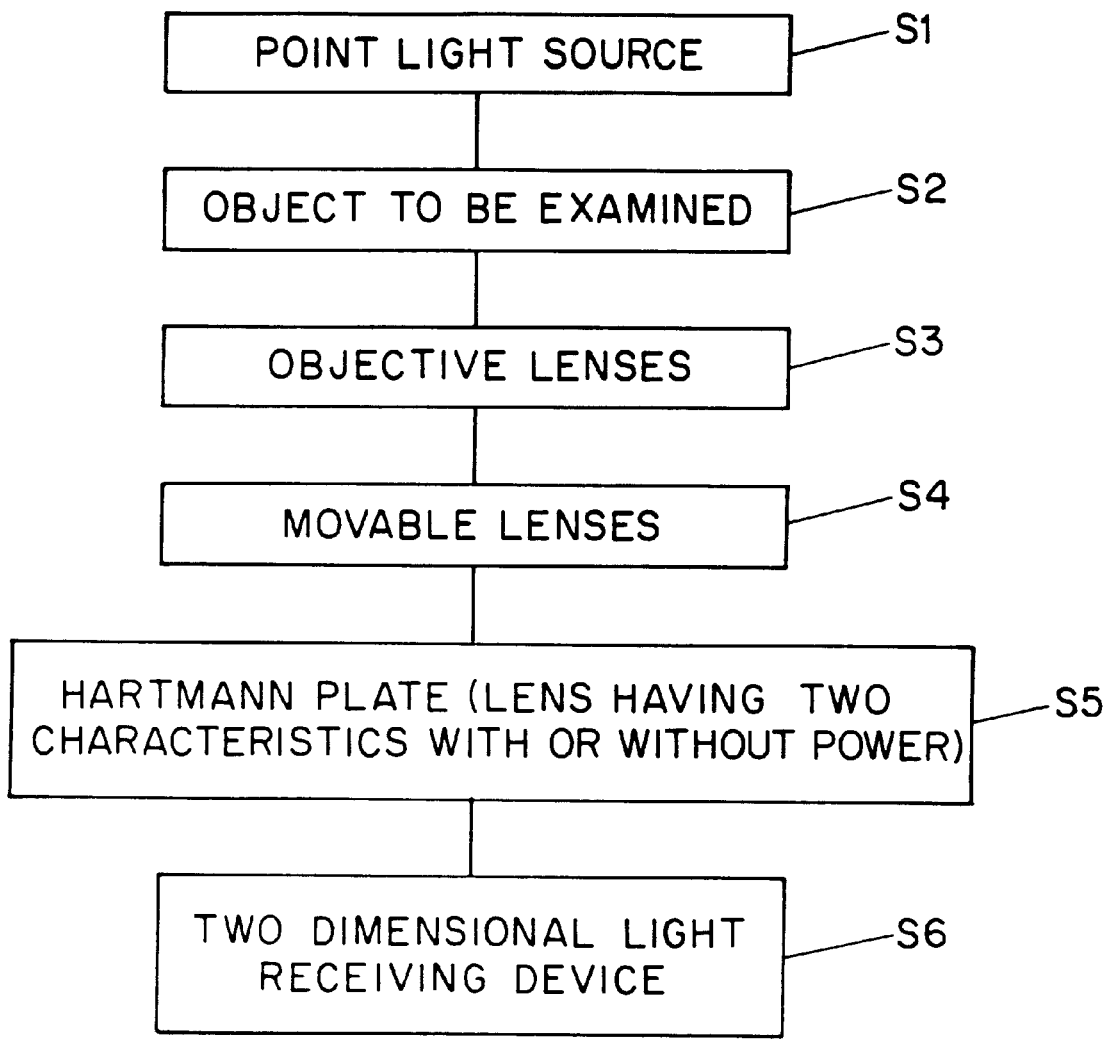

Described next, based on FIG. 7(a) and FIG. 7(b), is an alignment.

As shown in FIG. 7(a), if lenses, which exists at the side of a person to be examined with reference to movable lenses 302 in the light receiving system, are assumed to be objective lenses 301, the alignment can be achieved by locating the objective lenses 301 so that the front side focus thereof coincides with a measurement reference plane of the object to be examined (for example, an injection pupil or a conea surface when the object to be examined is a human eye).

The movable lenses 302 moves so that a front side focus of the movable lenses 302 comes to a point (which turns out to be a substantially conjugate point with reference to eyegrounds when the object to be examined is the human eye) at which a measuring light beam, after having passed through the objective lenses 301, intersects the optical axis. This allows substantially parallel light rays to be always launched into the light receiving device 500, thus making it possible to make a measurement region at the measurement reference plane substantially unchanged.

When the object to be examined is, for example, the human eye, an accurate position of a measuring light beam at a measurement reference plane of the front eye part can be obtained as follows. Based on a position at which the light beam passes through the converting member 400 and a position at which the light receiving device 500 receives the light beam, using interpolation method or extrapolation method, the light beam coordinate is determined at a conjugate point of the measurement reference plane of the front eye part after the movable lenses have passed, and then the light beam coordinate determined is divided by a transverse magnification of the optical system, thus obtaining the accurate position.

Described below, based on FIG. 7(*b*), is the operation.

At S1 (step 1, hereinafter abbreviated as S1), the light source 100 is switched on. Then, at S2, an object to be examined is fixed. Next, at S3, a front side focus position of the objective lenses 301 is made to coincide with the object to be examined. Still next, at S4, the movable lenses 302 are caused to move so that a front side focus of the movable lenses 302 coincides with an image of the light source 100. Moreover, at S5, the image is formed by making use of a zero-order light and a first-order light provided by the micro Fresnel lens (Hartmann plate) 400. Finally, at S6, the image formed at S5 is received, using a two dimensional light receiving device which is equivalent to the light receiving unit 500.

Additionally, as shown in FIG. 7(C), in the case of a lens meter, there is an effect of achieving the alignment with the use of marked points.

In the present first embodiment, the description is given taking a human eye as an object to be examined. The object to be examined, however, is not at all limited to the human eye, and the first embodiment makes it possible to measure optical characteristics of any object that is to be examined.

Furthermore, although the converting member 400 in the present first embodiment is configured to convert the reflected light rays into at least seventeen light beams, it is sufficient to employ a converting member which converts the reflected light rays into at least five light beams.

Second Embodiment

Figure 8:
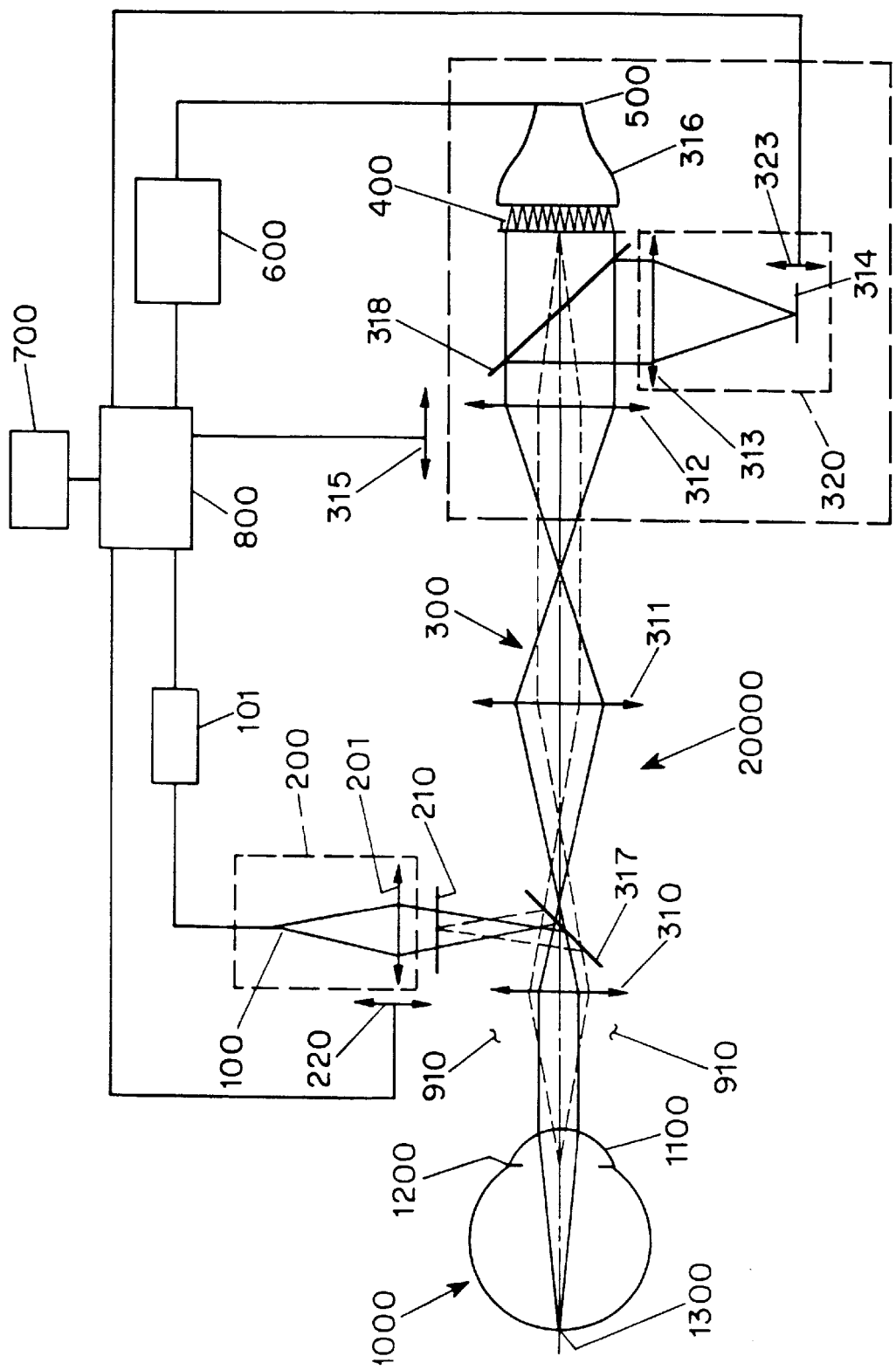
FIG. 8 is a diagram showing a configuration of an optical characteristic measuring apparatus 20000 according to a second embodiment of the present invention.

An optical characteristic measuring apparatus 20000 according to a second embodiment of the present invention, as shown in FIG. 8, comprises an illuminating light source 100, an illuminating optical system 200 for illuminating an infinitesimal domain on a retina of an eye to be examined with the use of light rays emitted from the light source 100, a light receiving optical system 300 for receiving light rays reflected back from the retina of the eye to be examined and guides the reflected light rays to a light receiving unit 500, a converting member 400 for converting the reflected light rays into at least seventeen light beams, the light receiving unit 500 for receiving a plurality of light rays converted at the converting member 400, an optical characteristic arithmetic unit 600 for determining optical characteristics of the eye to be examined 1000 on the basis of an inclination angle of the light rays obtained at the light receiving unit 500, and a control/arithmetic processing means 800 for performing a control of the whole apparatus.

Avoiding wavelength within the visible range, wavelength of, for example, substantially 840 nm is employed with the light source 100 in the present second embodiment. This makes it possible to carry out a measurement without making a person to be examined feel the measuring light beam.

The illuminating optical system 200 comprises a first condenser lens 201, a liquid crystal member 210, and a second luminous efficiency adjusting mechanism 220. The second luminous efficiency adjusting mechanism 220 is controlled in accordance with a signal from the control/arithmetic processing means 800, depending on a light-receiving level in the light receiving unit 500. The luminous efficiency adjustment is performed so that the light-receiving level in the light receiving unit becomes its maximum.

Figure 9:
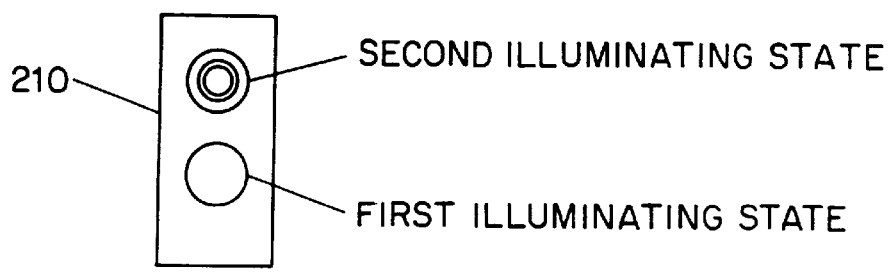
FIG. 9 is a diagram for explaining a liquid crystal member.

The liquid crystal member 210, as shown in FIG. 9, makes it possible to create a first illuminating state in which an aperture is formed in the vicinity of the center and a second illuminating state in which an aperture is formed in the vicinity of the periphery.

Regarding a configuration of a partial aperture in the liquid crystal member 210, it is characterized by being modified freely according to requirements from the optical system.

Figure 10:
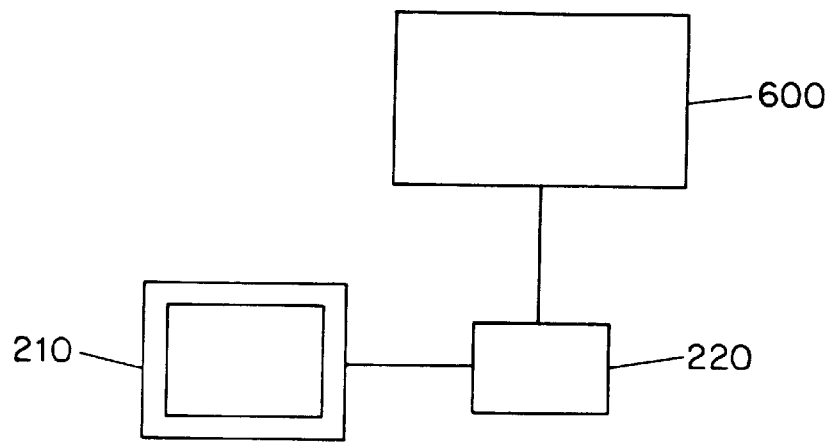
FIG. 10 is a diagram for explaining a driving configuration of the liquid crystal member.

Additionally, as shown in FIG. 10, the liquid crystal member 210 is configured to be driven through a liquid crystal driver by the control/arithmetic processing means 800.

The light receiving optical system 300 comprises a first measuring lens 310, a second measuring lens 311, a third measuring lens 312, a fixation point optical system 320, a third luminous efficiency adjusting mechanism 315, a tapered fiber handle 316, and a second beam splitter 318.

The fixation point optical system 320 comprises a fixation point lens 313, a fixation point 314, and an adjusting mechanism 323. The adjusting mechanism 323, based on a signal from the control/arithmetic processing means 800, causes the fixation point 314 to be integrally moved along an optical axis so that the fixation point 322 is located in a direction in which it is farther away from eyegrounds than a position conjugate with the eyegrounds, thus forming so-called a fogging state.

Incidentally, a first beam splitter 317 is configured so that it causes a light beam from the illuminating optical system 200 to be reflected back towards the eye to be examined 1000 and causes a light beam reflected from the eye to be examined 1000 to be transmitted.

The light receiving optical system 300 is configured to maintain a substantially conjugate relation between an iris 1200 of the eye to be examined 1000 and the light receiving unit 500 with reference to the first measuring lens 310 and the second measuring lens 311.

The conjugate relationship between the iris 1200 of the eye to be examined and the light receiving unit 500 is established by performing an adjustment so as to make appropriate an operating distance between the whole apparatus and the eye to be examined, i.e. a distance between the first measuring lens 310 and the eye to be examined 1000. Employed for accomplishing the task can be conventional and well-known many kinds of means.

Besides, the light receiving optical system 300 has an adjusting function of maintaining the substantially conjugate relation between the light receiving screen of the light receiving unit 500 and the iris 1200 of the eye to be examined 1000, and of making reflected light rays from the eyegrounds of the eye to be examined into substantially parallel light rays.

In the case of the present embodiment, a spherical component of the eye to be examined can be eliminated from objects to be examined on the light receiving unit 500 by integrally moving optical devices ranging from the third measuring lens 312 to the light receiving unit 500 and the fixation point optical system 320.

Accordingly, performed as follows is an operation of establishing the substantially conjugate relation between the eyegrounds 1300 of the eye to be examined and the light receiving screen of the light receiving unit 500. Namely, based on a signal which the control/arithmetic processing means 800 gives in correspondence with a spherical component S obtained by the optical characteristic arithmetic unit 600, the third luminous efficiency adjusting mechanism 315 causes the optical devices, which range from the third measuring lens 312 to the light receiving unit, to be integrally moved so that the spherical component S becomes its minimum, thus performing the operation.

In this case, in the illuminating optical system 200, the second luminous efficiency adjusting mechanism 220 and the third luminous efficiency adjusting mechanism 315 can be configured to be controlled independently. In some cases, it is sufficient to adjust either of the luminous efficiency adjusting mechanisms.

When the first measuring lens 310 and the second measuring lens 311 form an afocal optical system, it turns out that the optical devices, which range from the third measuring lens 312 to the light receiving unit, move in a coupled way with a movement of the illuminating optical system 200. Besides, since, depending on the magnification, the optical devices cover the same distance as the illuminating optical system 200 does, it is also possible to make the movement mechanism common to the both.

Incidentally, the movement made by the luminous efficiency adjusting mechanisms can also be performed in order to magnify a measurement width for a measurement of an extreme shortsightedness or farsightedness, or a measurement at a proximate point.

It is also possible to easily execute a conversion in magnification from the converting member 400 to the light receiving unit 500 by inserting the tapered fiber handle 316 between the converting member 400 and the light receiving unit 500.

In the optical characteristic arithmetic unit 600, in some cases, the spherical component of F (K, G, T, S, C, A, X, Y)=Constant (K)+Inclination (G, T, X, Y)+Spherical surface (S, X, Y)+Regular astigmatism (C, A, X, Y) (17) has been eliminated or made extremely small by moving the lenses in the light receiving optical system 300. In this case, the processing is performed, eliminating the spherical component from the polynomial. The method of processing is the same as that described in the first embodiment.

Before displaying the final result as refractive characteristics, magnitude of the spherical component is calculated using quantity of the movement of the lenses.

Also, depending on a setting or an arrangement of the optical system, there may be a case in which the movement of the lenses has not made the spherical component of the polynomial small enough to be negligible. In this case, the arithmetic calculation in the first embodiment is directly applied.

Before displaying the final result as refractive characteristics, magnitude of the spherical component is calculated using quantity of the movement of the lenses, and then the spherical component calculated is added to quantity of spherical component obtained by the polynomial approximation.

As is the case with the first embodiment, it is possible to perform, based on a signal from the light receiving unit 500, a measurement of the optical characteristics and an observation of the front eye part.

Concerning the other components and operations of the optical characteristic measuring apparatus 20000 according to the second embodiment configured above, they are the same as those of the optical characteristic measuring apparatus 10000 according to the first embodiment, and thus the description thereof will be omitted.

Figure 11:
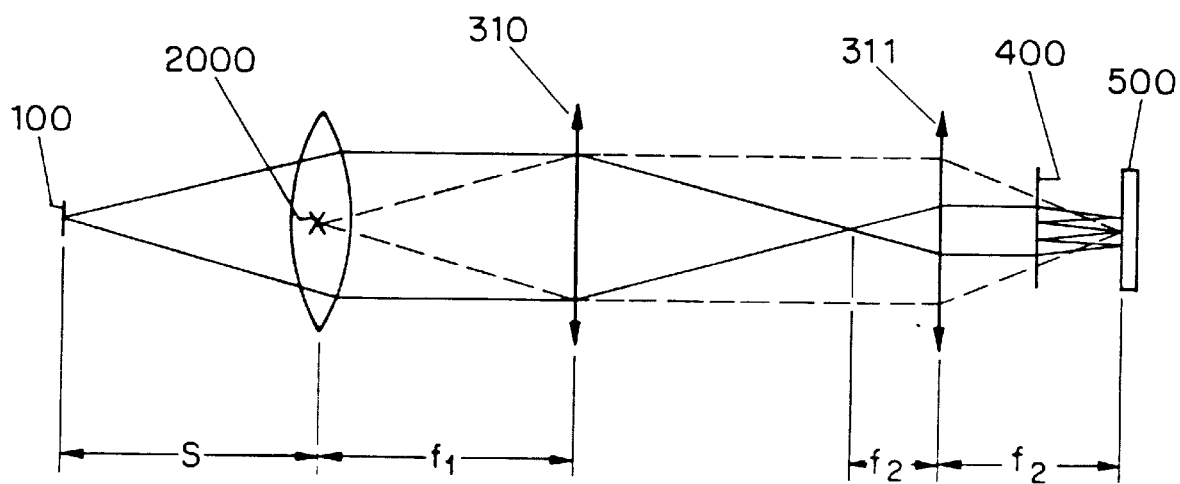
FIG. 11 is a diagram showing a modified embodiment.

Also, described below, based on FIG. 11, is a modified embodiment.

The present modified embodiment comprises a light source 100, a first measuring lens 310, a second measuring lens 311, a converting member 400, and a light receiving unit 500.

An object to be examined 2000 is located at a position of a front side focus of the first measuring lens 310. The light source 100 is in a conjugate relationship with a front side focus of the second measuring lens 311. The light receiving unit 500 is located at a position of a back side focus of the second measuring lens 311.

The converting member 400 is located $f_h$, i.e. a focal distance of a micro Fresnel lens provided therewith, ahead of the light receiving unit 500.

Incidentally, in FIG. 11, a full line shows a case in which a first-order light is employed, and a broken line shows a case in which an zero-order light is employed.

Also, since light beams of the other orders are blurred on a screen of the light receiving unit 500, it is preferable to perform the measurement using the first-order light and the zero-order light.

It is possible to calculate measurement values, as long as they are measurement values of a spherical component S, a cylindrical component C, and an axis angle component A, by using at least five points of data which consist of the point of origin and four points lying in different four radial directions. Moreover, if there is need of information on data which are at least one order higher than the five points of data, the number of the measuring points, through a summation of 2 * 8=16 and the point of origin, turns out to be at least seventeen or more.

Concerning the other components and operations of the optical characteristic measuring apparatus 20000 according to the second embodiment configured above, they are the same as those of the optical characteristic measuring apparatus 10000 according to the first embodiment, and thus the description thereof will be omitted.

In the present second embodiment, the description is given taking a human eye as an object to be examined. The object to be examined, however, is not at all limited to the human eye, and the second embodiment makes it possible to measure optical characteristics of any object that is to be examined.

Furthermore, although the converting member 400 in the present second embodiment is configured to convert the reflected light rays into at least seventeen light beams, it is sufficient to employ a converting member which converts the reflected light rays into at least five light beams.

The present invention configured above, when applied to a human eye, exhibits an excellent effect of making it possible to measure optical characteristics of refractive irregularities such as an irregular astigmatism as well as to observe portions such as a front eye part of the eye.

What is claimed is:

1. An optical characteristic measuring apparatus, comprising:

an illuminating light source;

an illuminating optical system for illuminating a minute area on a retina of an eye to be examined using light rays from said light source;

a light receiving optical system for receiving light rays reflected back from the retina of the eye to be examined and for guiding the reflected light rays to a light receiving unit;

a converting member for separating the reflected light rays into at least five regions and having a converging operation and a transmitting operation which, in said regions, converges the light rays and transmits the light rays, respectively;

a light receiving unit for receiving light rays converted by said converting member;

a front eye part displaying unit for forming an image of a front eye part of said eye to be examined on the basis of the light rays which have undergone the transmitting operation from said converting member and have been obtained at said light receiving unit; and an optical characteristic arithmetic unit for determining optical characteristics of the eye to be examined on the basis of an inclination angle of the light rays which have undergone the converging operation from said converting member and have been obtained at said light receiving unit.

2. The optical characteristic measuring apparatus as claimed in claim 1, wherein said converting member is configured to separate said reflected light rays into at least five regions and then diffract the light rays into a zero-order light beam and a first-order light beam.

3. The optical characteristic measuring apparatus as claimed in claim 1 or 2, wherein the number of the regions into which the reflected light rays are separated is seventeen instead of five.

4. The optical characteristic measuring apparatus as claimed in claim 1, wherein said converting member is configured by a plurality of double-focus micro Fresnel lenses located in a plane perpendicular to an optical axis.

5. The optical characteristic measuring apparatus as claimed in any one of claims 1 through 3, wherein said optical characteristic arithmetic unit determines an inclination angle of said reflected light rays from a position onto which the reflected light rays are converged on a light receiving screen of the light receiving unit by said plurality of micro Fresnel lenses, and determines, based on said inclination angle, optical characteristics of the eye to be examined.

6. The optical characteristic measuring apparatus as claimed in claim 1, wherein said light receiving optical system is configured so that there is established a substantially conjugate relation between an iris of the eye to be examined and said light receiving screen.

7. The optical characteristic measuring apparatus as claimed in claim 1, wherein said illuminating optical system is configured in such a manner that located around a point substantially conjugate with a pupil of the eye to be examined is a light rays-shielding member which forms a first illuminating state in which an illumination is performed through around a center of the pupil of the eye to be examined and a second illuminating state in which an illumination is performed through around a periphery of the pupil of the eye to be examined.

8. An optical characteristic measuring apparatus, comprising:

an illuminating light source;

an illuminating optical system for causing light rays from said light source to be directed to an object to be examined;

a light receiving optical system for receiving light rays reflected or refracted by the object to be examined and for guiding the reflected or refracted light rays to a light receiving unit;

a converting member for separating the reflected light rays into at least five regions and having a converging operation and a transmitting operation which, in said regions, converges the light rays and transmits the light rays, respectively;

a light receiving unit for receiving light rays converted by said converting member;

an object to be examined-displaying unit for forming an image of said object to be examined on the basis of the light rays which have transmitted from said converting member and have been obtained at said light receiving unit; and an optical characteristic arithmetic unit for determining optical characteristics of said object to be examined on the basis of an inclination angle of the light rays which have undergone the converging operation from said converting member and have been obtained at said light receiving unit.

9. The optical characteristic measuring apparatus as claimed in claim 8, wherein said converting member is configured to separate said reflected light rays into at least five regions and then diffract the light rays into a zero-order light beam and a first-order light beam.

10. The optical characteristic measuring apparatus as claimed in claim 8 or 9, wherein the number of the regions into which the reflected light rays are separated is seventeen instead of five.

* * * * *